(12) United States Patent
Haile et al.

(10) Patent No.: US 11,285,094 B2
(45) Date of Patent: Mar. 29, 2022

(54) NAIL COATING COMPOSITIONS AND METHODS HAVING POWDERED ACTIVATOR

(71) Applicants: Danny Lee Haile, La Habra, CA (US); Sunil Sirdesai, Irvine, CA (US); Kendra Gouse, Philadelphia, PA (US); Kevin Sheran, Haddonfield, NJ (US)

(72) Inventors: Danny Lee Haile, La Habra, CA (US); Sunil Sirdesai, Irvine, CA (US); Kendra Gouse, Philadelphia, PA (US); Kevin Sheran, Haddonfield, NJ (US)

( * ) Notice: Subject to any disclaimer, the term of this patent is extended or adjusted under 35 U.S.C. 154(b) by 0 days.

(21) Appl. No.: 16/523,873

(22) Filed: Jul. 26, 2019

(65) Prior Publication Data

US 2020/0030221 A1 Jan. 30, 2020

Related U.S. Application Data

(60) Provisional application No. 62/711,299, filed on Jul. 27, 2018.

(51) Int. Cl.

| *A61K 8/81* | (2006.01) |
|---|---|
| *A61K 8/34* | (2006.01) |
| *A61K 8/38* | (2006.01) |
| *A61K 8/41* | (2006.01) |
| *A61K 8/49* | (2006.01) |
| *A61Q 3/02* | (2006.01) |

(52) U.S. Cl.
CPC ............ *A61K 8/8147* (2013.01); *A61K 8/347* (2013.01); *A61K 8/38* (2013.01); *A61K 8/411* (2013.01); *A61K 8/4926* (2013.01); *A61K 8/4953* (2013.01); *A61K 8/8152* (2013.01); *A61Q 3/02* (2013.01); *A61K 2800/594* (2013.01)

(58) Field of Classification Search
None
See application file for complete search history.

(56) References Cited

U.S. PATENT DOCUMENTS

| 5,650,138 | A | * | 7/1997 | Resler | A61K 8/37 424/401 |
|---|---|---|---|---|---|
| 5,830,442 | A | * | 11/1998 | Beaver | A61Q 3/00 424/61 |
| 6,080,389 | A | * | 6/2000 | Sheariss | A45D 31/00 424/61 |
| 6,250,311 | B1 | * | 6/2001 | Megna | A45D 31/00 132/200 |

* cited by examiner

*Primary Examiner* — Kyung S Chang
(74) *Attorney, Agent, or Firm* — Blank Rome LLP

(57) ABSTRACT

Compositions, systems, kits and methods for forming a nail coating using a solid activator such as a powdered solid amine or solid component having an amine moiety. The powdered compositions may include a polymeric powder and a solid amine or solid component having an amine moiety. Systems and kits including the powdered composition and a liquid composition comprising a cyanoacrylate monomer are also provided. A method for forming a cosmetic nail coating using a solid activator is also provided. The method may include a) applying a liquid composition to a nail to form a wet nail, the liquid composition comprising a cyanoacrylate monomer, and b) applying to the wet nail a powdered composition, the powdered composition comprising a polymeric powder and a solid amine activator or solid component having an amine moiety.

5 Claims, No Drawings

NAIL COATING COMPOSITIONS AND METHODS HAVING POWDERED ACTIVATOR

CROSS-REFERENCE TO RELATED APPLICATIONS

This application claims the benefit of U.S. Provisional Application No. 62/711,299, entitled "Nail Coating Compositions and Methods Having Powdered Activator," filed on Jul. 27, 2018, which is incorporated by reference in its entirety, for all purposes, herein.

FIELD

The present disclosure is directed generally to nail coating compositions. More specifically, the present disclosure is directed to nail coating compositions having one or more activators in powdered form.

BACKGROUND

Enhancing the appearance of nails is an integral part of a woman's beauty regimen. One method to enhance the appearance of nails is to paint nail lacquer over natural nails. The resultant coating is formed by evaporation of the solvents from the cellulose-based formulation. Such coatings may only be used as overlays and may be removed by wiping the coating with acetone.

Another nail appearance enhancing method is to mix monomeric liquid (methacrylate monomers) with polymeric powder (methacrylate polymers with an initiator) to form a slurry. The slurry may be applied on a natural nail to form a coating by polymerization. This method may also be used to extend an existing nail or form an artificial nail enhancement. Such coatings may be painted using nail lacquer and may be removed by drilling or soaking them in acetone for about half an hour.

UV-LED cured gels (urethane acrylates with photoinitiator) may be used to form a coating over natural nails upon exposure to UV light. This method may also be used to extend natural nails. Such coatings may be painted with nail lacquer but must be removed by drilling. UV-LED cured soak-off gels (urethane acrylates with photoinitiator) are similar to UV-LED cured gels except that UV-LED cured soak-off gels can be soaked-off in acetone as they are lightly cross-linked. These gels are colored, so they form a colored coating over natural nails eliminating the need for polishing the nails with nail lacquer. This method may be used for preparing overlays only.

Polygel coatings are a loosely-defined hybrid coating that encompasses attributes of the two preceding methods. It is a relatively new category of artificial nails in the nail-beauty industry and forms coatings upon exposure to UV that may only be removed through drilling. This method may also be used to extend existing nails. Snap-on nail tips is a method where a pre-formed plastic nail tip is glued to the edge of the natural nail. Then a layer is applied over the natural nail and artificial tip. The layer may be formed by any of the previously described methods. The snap-on nail tip method is used to extend existing nails only.

A method often preferred by women seeking to beautify their own nails, as well as less accomplished manicurists, includes wetting the natural nail with a cyanoacrylate monomer liquid followed by dipping the wetted nail in a colored or uncolored polymeric powder. The polymeric powder acts as a filler and provides strength to the coating as well as other aesthetic benefits. Finally, an activator, such as an active amine compound formulated in a solvent, is applied to the nail in order to cure the coating by accelerating the polymerization of the cyanoacrylate monomer. This method is substantially faster than other methods and often provides a desirable look. However, a disadvantage of the technique is that different rates of curing or polymerization may occur throughout the coating if the activator is not applied evenly and rapidly enough. In such circumstances, premature chipping may occur and an uneven gloss may result. Additionally, solvent evaporation from the applicator bottle containing the activator may result in increased concentration of activator in the formulation and the corresponding application of too much activator to the nail will result in a coating that is brittle and prone to chipping.

Accordingly, cosmetic nail coating compositions having one or more advantageous characteristics and/or that overcome the problems associated with the application of liquid activators to cyanoacrylate monomer compositions are desirable.

SUMMARY

The present disclosure provides compositions, systems, and methods for forming a cosmetic nail coating that include a solid activator in powdered form that may be used to cure cyanoacrylate monomer nail compositions. The solid activator may be included, for example, in the polymeric powder contacted with the cyanoacrylate monomer wetting liquid to form a nail coating, thereby eliminating the need for a separate activator application step. In at least some instances, the solid activator is a solid amine or solid component having an amine moiety in powdered form and the polymeric powder may be a methacrylate polymeric powder. For example, the solid amine or a solid component having an amine moiety in powdered form may be blended into the polymeric powder. When the wet cyanoacrylate monomer liquid contacts the polymeric powder blended with solid amine moiety, the amine active immediately triggers the polymerization of the cyanoacrylate monomer resulting in a gleaming coating.

The use of a solid activator evenly dispersed in the polymeric powder provides for uniform polymerization of the cyanoacrylate monomer not otherwise achievable using liquid activator application. Accordingly, nail coatings formed using the presently disclosed compositions have properties, such as durability and resistance to chipping, that are superior to similar compositions formed using a liquid activator compositions or methods. The presently disclosed methods, systems, and compositions having solid amine or solid component having an amine moiety activators provide for nail coatings with reduced incidences of non-uniform coating and uneven gloss in cyanoacrylate monomer-methacrylate polymer powder compositions. The presently disclosed compositions also reduce the number of application steps required for forming (meth)acrylate polymeric powder nail coatings. Additionally, the presently disclosed compositions and methods provide for nail coatings having increased integrity, thereby increasing the confidence of the technician or user applying the coating to the nail.

DETAILED DESCRIPTION

For illustrative purposes, the principles of the present disclosure are described by referencing various exemplary embodiments thereof. Although certain embodiments of the present disclosure are specifically described herein, one of ordinary skill in the art will readily recognize that the same principles are equally applicable to, and can be employed in other compositions and methods. Before explaining the disclosed embodiments of the present disclosure in detail, it is to be understood that the present disclosure is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

As used herein and in the appended claims, the singular forms "a", "an", and "the" include plural references unless the context clearly dictates otherwise. The singular form of any class of the ingredients or components refer not only to one chemical species within that class, but also to a mixture of those chemical species; for example, the term "solid amine" in the singular form, may refer to a mixture of compounds each of which is also a solid amine. The terms "a" (or "an"), "one or more" and "at least one" can be used interchangeably herein. It is also to be noted that the terms "comprising," "including," and "having" can be used interchangeably.

The abbreviations and symbols as used herein, unless indicated otherwise, take their ordinary meaning. The abbreviation or symbol "µm" means micron or micrometer.

The term "wt %" means percent by weight. The phrase "wherein the solid amine comprises from about 0.5 wt % to about 25 wt % of the powdered composition" means that the recited percent by weight values for each ingredient is compared to the entire powdered composition. For example, the entire powdered composition includes not only ingredients which wt % are listed, but also listed ingredients for which wt % are omitted, and also ingredients that may not be recited.

The term "client" refers to a person whose nails are being treated. The phrase "nail technician" or "technician" is a worker skilled or licensed in the art of providing nail extensions, artificial nails, acrylic nails, gel nails, and other manicure services for clients. Alternative names for a nail technician may include a manicurist, or a cosmetologist. Such a person may work for pay at a nail salon, or may be a manicure aficionado.

Under one embodiment of the present invention, the client and the nail technician are two different individuals. Although the present disclosure describes the nail technician and the client as two separate individuals, it is understood that the claimed compositions and methods are also suitable for use by a single person who is both a nail technician and a client. Under another embodiment of the present disclosure, the client and the nail technician are the same person.

The term "nail," refers to either a fingernail or a toenail. The term "nail" also refers to a human nail, as well as to any toughened keratin at the end of a digit of a nonhuman animal. The terms "coating" and "nail coating," in all there forms, including as in "cosmetic nail coating," refers to the hardened, fully cured substance covering a part or all of the nail, and any portions of this substance that extends or is built beyond the free edge of the nail.

The term "powder," in all its forms, including "in powder form," refers to a composition comprising solid particles that is substantially free of solvent. Therefore, the term "powder" excludes compositions that comprise solids suspended or dissolved in a solvent.

The definition of the term "(meth)acrylate" as referred to in the monomeric form includes an ester, a salt, or a conjugate base of methacrylic acid, with the formula $CH_2=C(CH_3)-COO^-$.

The term "(meth)acrylate" means acrylate, methacrylate, or a mixture thereof. When referring to a compound, "(meth)acrylate" means an ester, a salt, or a conjugate base of an acrylic acid, with the formula $CH_2=C(R)-COO^-$, wherein R is H, Me, or a mixture thereof. By extension, a monomer or polymer name containing as a part of its term the string "(meth)acrylate" should be interpreted as referring to the same monomer or polymer, that is an acrylate, methacrylate, or a mixture thereof. For example, the term "poly($C_{1-12}$alkyl (meth)acrylate)" means "any of poly($C_{1-12}$alkyl acrylate), poly($C_{1-12}$alkyl methacrylate), and a mixture of poly($C_{1-12}$alkyl acrylate) and poly($C_{1-12}$alkyl methacrylate)."

According to at least one aspect of the present disclosure, a powdered composition for forming a nail coating is provided. The composition may include a polymeric powder and a solid activator. In at least some instances, the solid activator may be milled and then blended with the polymeric powder. The polymeric powder acts as a filler and provides strength to the coating. The polymeric powder may be a (meth)acrylate polymeric powder. For example, the polymeric powder may include polyethyl methacrylate (PEMA), polymethyl methacrylate (PMMA), polyethyl acrylate, polymethyl acrylate, and any combination thereof. In some instances, the polymeric powder may be a mixture of PEMA and PMMA. In some instances, the polymeric powder may include benzoyl peroxide powder. In at least some instances, the benzoyl peroxide powder may serve as an initiator that aids in polymerization of the cyanoacrylate monomer. In some cases, the rise in temperature coincident with cyanoacrylate polymerization may cause disassociation of BPO into BPO free radicals which may facilitate polymerization.

The polymeric powder may also include one or more pigments in order to achieve a desired aesthetic look. In some instances, a colorant or special effects pigment may be included in the polymeric powder. One purpose of using pigment in the powdered composition is to provide a tint or a color to the formed cosmetic nail coating. The use of such color in the powdered composition may allow the technician to omit certain selected post treatment steps after the formation of the cosmetic nail coating.

Another purpose of using a pigment is to give a clear or colorless or whitish appearance of the cosmetic nail coating. The pigment may be used to address any yellowing of the cosmetic nail coating. Yet another purpose of using a pigment is to provide a whitish appearance to the powdered composition, so that it appears as an attractive, clean product to the nail technician.

Examples of pigments that may be incorporated into the powdered composition of the present disclosure include: annatto, caramel, carmine, B-carotene, potassium sodium copper chlorophyllin (chlorophyllin copper-complex), dihydroxyacetone, bismuth oxychloride, guaiazulene, iron oxides, ferric ammonium ferrocyanide, ferric ferrocyanide, chromium hydroxide green, chromium oxide greens, guanine, pyrophyllite, mica, silver, titanium dioxide, aluminum powder, bronze powder, copper powder, ultramarines, manganese violet, zinc oxide, luminescent zinc sulfide, FD&C Blue No. 1, D&C Blue No. 4, Iron Blue, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, D&C Violet No. 2, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10, D&C Yellow No. 11, and any mixture of the foregoing. As will be recognized by the practitioner of the art, some of the pigments in the above list are better suited for use in the powdered composition than others, because they offer better composition stability of the powdered composition, and they do not interfere with the curing process.

Under at least one embodiment of the present disclosure, the powdered composition comprises a pigment is selected from the group consisting of ultramarine, manganese violet, zinc oxide, FD&C Blue No. 1, D&C Blue No. 4, Iron Blue, D&C Violet No. 2, and any mixture thereof.

Special effects pigment may be any pigment that gives either the powdered composition or the formed cured composition a special effect, such as an increased pearlescent, iridescent, shimmering, transparency or complex effects. Examples of special effect pigments include titanated micas, mica based interference colors, mica coated with titanium dioxide and iron oxide, mica based gold pearls, mica based metallic pearls, mica based pearl pigments, bismuth oxychloride, synthetic mica based interference pearls, synthetic mica based white pigment, silicate based pearls, titanium oxide and tin oxide on silicate platelets, flaked aluminum powder, silver coated silicate flakes, and any combination of the foregoing.

The powdered composition also includes a solid activator. The solid activator cures a nail coating once contacted with a cyanoacrylate monomer wetting liquid. The solid activator may be a solid amine or a solid component having an amine moiety. The solid amine or solid component having an amine moiety cures the nail coating by accelerating the polymerization of the cyanoacrylate monomer once contacted with a cyanoacrylate monomer wetting liquid. In at least some instances, the solid amine or a solid component having an amine moiety may be milled and then blended with the polymeric powder. In at least some instances, the solid amine or a solid component having an amine moiety may be benzyl aniline, diamino hexane, toluidine, dichloroaniline, anisidine, bromoaniline, 2-amino, 4-picoline, phenylene diamine, dihydroxy ethyl p-toluidine, barbituric acid, derivatives of barbituric acid, and any combination thereof. According to at least one aspect of the present disclosure, the powdered composition forms a nail coating when contacted with a liquid composition comprising a cyanoacrylate monomer and a solvent.

The solid amine or a solid component having an amine moiety may be milled so that the solid amine comprises an average particle size having advantageous characteristics when blended with the polymeric powder to form the powdered composition. For instance, the powdered composition has an advantageous shelf-life and solid amine or solid component having an amine moiety retains effectiveness to catalyze the polymerization of cyanoacrylate monomer when contacted with a wetting liquid comprising cyanoacrylate monomer for periods of time suitable for commercial use. Additionally, the solid amine or solid component having an amine moiety may be milled so as to impart a desirable cure rate during use.

In some cases, the solid amine or solid component having an amine moiety may be a powder characterized by an average particles size of from about 1 µm to about 500 µm, or from about 10 µm to about 50 µm, or from about 25 µm to about 250 µm, or from about 100 µm to about 300 µm. In some instances, the solid amine or solid component having an amine moiety may be a powder characterized by an average particle size that is less than about 500 µm, or less than about 250 µm, or less than about 100 µm, or less than about 50 µm, or less than about 30 µm, or less than about 20 µm, or less than about 10 µm. In at least some instances, the average particle size of the solid amine or solid component having an amine moiety is the same or smaller than the average particle size of the polymeric powder.

In at least some instances, the solid amine or solid component having an amine moiety may comprise from about 0.1 wt % to about 5 wt % of the powdered composition, or from about 0.2 wt % to about 0.6 wt %, or from about 0.25 wt % to about 0.5 wt %, or from about 0.1 wt % to about 2.5%, or from about 0.1 wt % to about 1 wt % of the powdered composition. In some cases, the polymeric powder comprises from about 95 wt % to about 99.9 wt % of the powdered composition, or from about 99.4 wt % to about 99.8 wt %, or from about 99.5 wt % to about 99.75 wt %, or from about 97.5 wt % to about 99.9 wt %, or from about 99.0 wt % to about 99.9 wt %, or from about 75 wt % to about 99.5 wt %, or from about 65 wt % to about 95 wt %, or from about 55 wt % to about 99 wt % of the powdered composition.

According to at least one aspect of the present disclosure, a system for forming a nail coating is provided. The system may include a powdered composition comprising a polymeric powder and a solid amine. The system may further include a liquid composition comprising a cyanoacrylate monomer and a solvent. When the powdered composition of the system is contacted with the liquid composition of the system a nail coating is formed.

The liquid composition included in the system may include a cyanoacrylate monomer selected from the group consisting of ethyl cyanoacrylate, propyl cyanoacrylate, iso-propyl cyanoacrylate, butyl cyanoacrylate, iso-butyl cyanoacrylate, and any combination thereof.

The liquid composition may further include an inhibitor. The inhibitor may be, for example, hydroquinone, butylated hydroxyl toluene, methoxy hydroquinone, and any combination thereof. The liquid composition may also further include a thickener. For example, a thickener may be added to the liquid composition to achieve a desired viscosity. The thickener may be, for example, polyethyl methacrylate, polymethyl methacrylate, polyethyl acrylate, polymethyl acrylate, and any combination thereof.

The powdered composition included in the system may be the same powdered composition described above. For example, the powdered composition may include a polymeric powder and a solid amine. In at least some instances, the solid amine may be milled and then blended with the polymeric powder. In at least some instances, the solid amine may be benzyl aniline, diamino hexane, toluidine, dichloroaniline, anisidine, bromoaniline, 2-amino, 4-picoline, phenylene diamine, dihydroxy ethyl p-toluidine, barbituric acid, derivatives of barbituric acid, and any combination thereof. The solid amine may be a powder characterized by an average particles size of from about 1 µm to about 500 µm, or from about 10 µm to about 50 µm, or from about 25 µm to about 250 µm, or from about 100 µm to about 300 µm. In some instances, the solid amine may be a powder characterized by an average particle size that is less than about 500 µm, or less than about 250 µm, or less than about 100 µm, or less than about 50 µm, or less than about 30 µm, or less than about 20 µm, or less than about 10 µm.

In at least some instances, the solid amine may or solid component having an amine moiety may comprise from about 0.1 wt % to about 5 wt % of the powdered composition, or from about 0.2 wt % to about 0.6 wt %, or from about 0.25 wt % to about 0.5 wt %, or from about 0.1 wt % to about 2.5%, or from about 0.1 wt % to about 1 wt % of the powdered composition. In some cases, the polymeric powder may comprise from about 95 wt % to about 99.9 wt % of the powdered composition, or from about 99.4 wt % to about 99.8 wt %, or from about 99.5 wt % to about 99.75 wt %, or from about 97.5 wt % to about 99.9 wt %, or from about 99.0 wt % to about 99.9 wt %, or from about 75 wt % to about 99.5 wt %, or from about 65 wt % to about 95 wt %, or from about 55 wt % to about 99 wt % of the powdered composition.

The powdered composition in the system also includes a polymeric powder. The polymeric powder may be a (meth)acrylate polymeric powder. For example, the polymeric powder may include polyethyl methacrylate (PEMA), polymethyl methacrylate (PMMA), polyethyl acrylate, polymethyl acrylate, and any combination thereof. In some instances, the polymeric powder may be a mixture of PEMA and PMMA. In some instances, the polymeric powder may include benzoyl peroxide powder. The polymeric powder may also include one or more pigments in order to achieve a desired aesthetic look.

In at least some instances, the system excludes an activator in liquid form. For example, the presently disclosed kits may not contain a liquid amine activator.

According to one aspect of the present disclosure, a kit is provided. The kit may include a first container containing a powdered composition and a second container containing a liquid composition. The powdered composition may include a polymeric powder and a solid amine while the liquid composition may include cyanoacrylate monomer. When the powdered composition in the first container is contacted with the liquid composition in the second container a nail coating is formed.

The liquid composition included in the kit may include a cyanoacrylate monomer selected from the group consisting of ethyl cyanoacrylate, propyl cyanoacrylate, iso-propyl cyanoacrylate, butyl cyanoacrylate, iso-butyl cyanoacrylate, and any combination thereof. The liquid composition may further include an inhibitor. The inhibitor may be, for example, hydroquinone, butylated hydroxyl toluene, methoxy hydroquinone, and any combination thereof. The liquid composition may also further include a thickener. The thickener may be, for example, polyethyl methacrylate, polymethyl methacrylate, polyethyl acrylate, polymethyl acrylate, and any combination thereof.

The powdered composition included in the kit may be the same powdered composition described above. For example, the powdered composition may include a polymeric powder and a solid amine. In at least some instances, the solid amine or solid component having an amine moiety may be milled and then blended with the polymeric powder. In at least some instances, the solid amine or solid component having an amine moiety may be benzyl aniline, diamino hexane, toluidine, dichloroaniline, anisidine, bromoaniline, 2-amino, 4-picoline, phenylene diamine, dihydroxy ethyl p-toluidine, barbituric acid, derivatives of barbituric acid, and any combination thereof. The solid amine or solid component having an amine moiety may be a powder characterized by an average particles size of from about 1 μm to about 500 μm, or from about 10 μm to about 50 μm, or from about 25 μm to about 250 μm, or from about 100 μm to about 300 μm. In some instances, the solid amine may be a powder characterized by an average particle size that is less than about 500 μm, or less than about 250 μm, or less than about 100 μm, or less than about 50 μm, or less than about 30 μm, or less than about 20 μm, or less than about 10 μm.

In at least some instances, the solid amine may or solid component having an amine moiety may comprise from about 0.1 wt % to about 5 wt % of the powdered composition, or from about 0.2 wt % to about 0.6 wt %, or from about 0.25 wt % to about 0.5 wt %, or from about 0.1 wt % to about 2.5%, or from about 0.1 wt % to about 1 wt % of the powdered composition. In some cases, the polymeric powder may comprise from about 95 wt % to about 99.9 wt % of the powdered composition, or from about 99.4 wt % to about 99.8 wt %, or from about 99.5 wt % to about 99.75 wt %, or from about 97.5 wt % to about 99.9 wt %, or from about 99.0 wt % to about 99.9 wt %, or from about 75 wt % to about 99.5 wt %, or from about 65 wt % to about 95 wt %, or from about 55 wt % to about 99 wt % of the powdered composition.

The powdered composition in the kit also includes a polymeric powder. The polymeric powder may be a (meth)acrylate polymeric powder. For example, the polymeric powder may include polyethyl methacrylate (PEMA), polymethyl methacrylate (PMMA), polyethyl acrylate, polymethyl acrylate, and any combination thereof. In some instances, the polymeric powder may be a mixture of PEMA and PMMA. In some instances, the polymeric powder may include benzoyl peroxide powder. The polymeric powder may also include one or more pigments in order to achieve a desired aesthetic look.

In at least some instances, the kit excludes an activator in liquid form. For example, the presently disclosed kits may not contain a liquid amine activator.

According to an aspect of the present disclosure, a method for forming a cosmetic nail coating is provided. The method may include a) applying a liquid composition that includes a cyanoacrylate monomer to a nail to form a wet nail. The method may further include b) applying to the wet nail a powdered composition that includes a polymeric powder and a solid amine activator. For example, the wet nail may be dipped in the powdered composition. In other cases, the powdered composition may sprinkled on the wet nail. Once the powdered composition comprising a solid amine or a solid component having an amine moiety activator contacts the cyanoacrylate monomer wetting liquid, the solid amine or a solid component having an amine moiety activator causes the cyanoacrylate monomer to polymerize thereby curing the cosmetic nail coating. The method may further include repeating steps a) and b) until a coating having a desired thickness is achieved.

In at least some instances, the method excludes the application of an activator, such as an amine activator, in liquid form. Instead, the presently disclosed methods involve the application of a solid amine to the nail in powdered form.

The liquid composition included in the method may include a cyanoacrylate monomer selected from the group consisting of ethyl cyanoacrylate, propyl cyanoacrylate, iso-propyl cyanoacrylate, butyl cyanoacrylate, iso-butyl cyanoacrylate, and any combination thereof. The liquid composition used in the method may further include an inhibitor. The inhibitor may be, for example, hydroquinone, butylated hydroxyl toluene, methoxy hydroquinone, and any combination thereof. The liquid composition may also further include a thickener. The thickener may be, for example, polyethyl methacrylate, polymethyl methacrylate, polyethyl acrylate, polymethyl acrylate, and any combination thereof.

The powdered composition included in the method may be the same powdered composition described above. For example, the powdered composition may include a polymeric powder and a solid amine or solid component having an amine moiety. In at least some instances, the solid amine or solid component having an amine moiety may be milled and then blended with the polymeric powder. In at least some instances, the solid amine may be benzyl aniline, diamino hexane, toluidine, dichloroaniline, anisidine, bromoaniline, 2-amino, 4-picoline, phenylene diamine, dihydroxy ethyl p-toluidine, barbituric acid, derivatives of barbituric acid, and any combination thereof. The solid amine or solid component having an amine moiety may be a powder characterized by an average particles size of from about 1 µm to about 500 µm, or from about 10 µm to about 50 µm, or from about 25 µm to about 250 µm, or from about 100 µm to about 300 µm. In some instances, the solid amine may be a powder characterized by an average particle size that is less than about 500 µm, or less than about 250 µm, or less than about 100 µm, or less than about 50 µm, or less than about 30 µm, or less than about 20 µm, or less than about 10 µm.

In at least some instances, the solid amine may or solid component having an amine moiety may comprise from about 0.1 wt % to about 5 wt % of the powdered composition, or from about 0.2 wt % to about 0.6 wt %, or from about 0.25 wt % to about 0.5 wt %, or from about 0.1 wt % to about 2.5%, or from about 0.1 wt % to about 1 wt % of the powdered composition. In some cases, the polymeric powder may comprise from about 95 wt % to about 99.9 wt % of the powdered composition, or from about 99.4 wt % to about 99.8 wt %, or from about 99.5 wt % to about 99.75 wt %, or from about 97.5 wt % to about 99.9 wt %, or from about 99.0 wt % to about 99.9 wt %, or from about 75 wt % to about 99.5 wt %, or from about 65 wt % to about 95 wt %, or from about 55 wt % to about 99 wt % of the powdered composition.

The powdered composition in the method also includes a polymeric powder. The polymeric powder may be a (meth) acrylate polymeric powder. For example, the polymeric powder may include polyethyl methacrylate (PEMA), polymethyl methacrylate (PMMA), polyethyl acrylate, polymethyl acrylate, and any combination thereof. In some instances, the polymeric powder may be a mixture of PEMA and PMMA. In some instances, the polymeric powder may include benzoyl peroxide powder. The polymeric powder may also include one or more pigments in order to achieve a desired aesthetic look.

EXAMPLES

Example 1

Benzyl aniline is milled to produce benzyl aniline having an average particle size suitable for activating a cyanoacrylate monomer wetting liquid to form a cosmetic nail coating. The milled benzyl aniline will is then blended with a (meth)acrylate polymeric powder consisting of a mixture of polyethyl methacrylate (PEMA) and polymethyl methacrylate (PMMA) to form a powdered composition suitable for forming a nail coating.

Example 2

A fingernail is prepared by removing oils from the nail by applying a low boiling point solvent to the nail and wiping away the residual solvent. The nail is then wetted with a cyanoacrylate monomer liquid. The powdered composition of Example 1 is then applied to the wetted nail by dipping the nail into the powdered composition of Example 1 thereby curing the nail to form a nail coating of good durability and aesthetic appeal. The cyanoacrylate monomer liquid is then reapplied to the coated nail and cured by application of the powdered composition containing the solid amine (benzyl aniline) in order to deposit a second layer of nail coating on top of the first layer in order to provide added depth to the cosmetic nail coating.

STATEMENTS OF THE DISCLOSURE

Numerous examples are provided herein to enhance understanding of the present disclosure. A specific set of statements are provided as follows.

Statement 1: A powdered composition for forming a nail coating, the composition comprising: a polymeric powder; and a solid amine or a solid component having an amine moiety.

Statement 2: A composition according to Statement 1, wherein the solid amine or a solid component having an amine moiety is selected from the group consisting of benzyl aniline, diamino hexane, toluidine, dichloroaniline, anisidine, bromoaniline, 2-amino, 4-picoline, phenylene diamine, dihydroxy ethyl p-toluidine, barbituric acid, derivatives of barbituric acid, and any combination thereof.

Statement 3: A composition according to Statement 1 or Statement 2, wherein the polymeric powder is a (meth) acrylate polymeric powder.

Statement 4: A composition according to any one of the preceding Statements 1-3, wherein the polymeric powder is selected from the group consisting of polyethyl methacrylate, polymethyl methacrylate, polyethyl acrylate, polymethyl acrylate, and any combination thereof.

Statement 5: A composition according to any one of the preceding Statements 1-4, wherein the polymeric powder comprises benzoyl peroxide powder.

Statement 6: A composition according to any one of the preceding Statements 1-4, further comprising benzoyl peroxide powder.

Statement 7: A composition according to any one of the preceding Statements 1-6, further comprising one or more pigments.

Statement 8: A composition according to any one of the preceding Statements 1-6, wherein the polymeric powder comprises one or more pigments.

Statement 9: A composition according to any one of the preceding Statements 1-8, wherein the solid amine or a solid component having an amine moiety is milled and then blended with the polymeric powder.

Statement 10: A composition according to any one of the preceding Statements 1-9, wherein the solid amine or a solid component having an amine moiety comprises a powder characterized by an average particle size of from about 1 µm to about 500 µm.

Statement 11: A composition according to any one of the preceding Statements 1-9, wherein the solid amine or a solid component having an amine moiety comprises a powder characterized by an average particle size of from about 10 µm to about 50 µm.

Statement 12: A composition according to any one of the preceding Statements 1-9, wherein the solid amine or a solid component having an amine moiety comprises a powder characterized by an average particle size that is less than about 50 µm.

Statement 13: A composition according to any one of the preceding Statements 1-9, wherein the solid amine or a solid component having an amine moiety comprises a powder characterized by an average particle size that is less than about 30 µm.

Statement 14: A composition according to any one of the preceding Statements 1-9, wherein the solid amine or a solid component having an amine moiety comprises a powder characterized by an average particle size that is less than about 20 µm.

Statement 15: A composition according to any one of the preceding Statements 1-9, wherein the solid amine or a solid component having an amine moiety comprises a powder characterized by an average particle size that is less than about 10 µm.

Statement 16: A composition according to any one of the preceding Statements 1-15, wherein when the composition forms a nail coating when contacted with a liquid composition comprising a cyanoacrylate monomer.

Statement 17: A composition according to any one of the preceding Statements 1-16, wherein the solid amine or a solid component having an amine moiety comprises from about 0.1 wt % to about 5 wt % of the powdered composition.

Statement 18: A composition according to any one of the preceding Statements 1-16, wherein the solid amine or a solid component having an amine moiety comprises from about 0.1 wt % to about 1 wt % of the powdered composition.

Statement 19: A composition according to any one of the preceding Statements 1-16, wherein the solid amine or a solid component having an amine moiety comprises from about 0.2 wt % to about 0.6 wt % of the powdered composition.

Statement 20: A composition according to any one of the preceding Statements 1-16, wherein the solid amine or a solid component having an amine moiety comprises from about 0.25 wt % to about 0.6 wt % of the powdered composition.

Statement 21: A composition according to any one of the preceding Statements 1-16, wherein the solid amine or a solid component having an amine moiety comprises from about 0.1 wt % to about 2.5 wt % of the powdered composition.

Statement 22: A composition according to any one of the preceding Statements 1-21, wherein the polymeric powder comprises from about 95 wt % to about 99.9 wt % of the powdered composition.

Statement 23: A composition according to any one of the preceding Statements 1-21, wherein the polymeric powder comprises from about 99.4 wt % to about 99.8 wt % of the powdered composition.

Statement 24: A composition according to any one of the preceding Statements 1-21, wherein the polymeric powder comprises from about 99.5 wt % to about 99.75 wt % of the powdered composition.

Statement 25: A composition according to any one of the preceding Statements 1-21, wherein the polymeric powder comprises from about 97.5 wt % to about 99.9 wt % of the powdered composition.

Statement 26: A composition according to any one of the preceding Statements 1-21, wherein the polymeric powder comprises from about 99.0 wt % to about 99.9 wt % of the powdered composition.

Statement 27: A composition according to any one of the preceding Statements 1-21, wherein the polymeric powder comprises from about 75 wt % to about 99.5 wt % of the powdered composition.

Statement 28: A composition according to any one of the preceding Statements 1-21, wherein the polymeric powder comprises from about 65 wt % to about 95 wt % of the powdered composition.

Statement 29: A composition according to any one of the preceding Statements 1-21, wherein the polymeric powder comprises from about 55 wt % to about 99 wt % of the powdered composition.

Statement 30: A system for forming a nail coating, the system comprising: a powdered composition comprising a polymeric powder and a solid amine or a solid component having an amine moiety; and a liquid composition comprising a cyanoacrylate monomer; wherein when the powdered composition is contacted with the liquid composition a nail coating is formed.

Statement 31: A system according to Statement 30, wherein the cyanoacrylate monomer is selected from the group consisting of ethyl cyanoacrylate, propyl cyanoacrylate, iso-propyl cyanoacrylate, butyl cyanoacrylate, iso-butyl cyanoacrylate, and any combination thereof.

Statement 32: A system according to Statement 30 or Statement 31, wherein the cyanoacrylate monomer comprises from about 95 wt % to about 99.75 wt % of the liquid composition.

Statement 33: A system according to any one of the preceding Statements 30-32, wherein the liquid composition further comprises an inhibitor selected from the group consisting of hydroquinone, butylated hydroxyl toluene, methoxy hydroquinone, and any combination thereof.

Statement 34: A system according to any one of the preceding Statements 30-33, wherein the liquid composition further comprises a thickener selected from the group consisting of polyethyl methacrylate, polymethyl methacrylate, polyethyl acrylate, polymethyl acrylate, and any combination thereof.

Statement 35: A system according to any one of the preceding Statements 30-34, wherein the solid amine or a solid component having an amine moiety is selected from the group consisting of benzyl aniline, diamino hexane, toluidine, dichloroaniline, anisidine, bromoaniline, 2-amino, 4-picoline, phenylene diamine, dihydroxy ethyl p-toluidine, barbituric acid, derivatives of barbituric acid, and any combination thereof.

Statement 36: A system according to any one of the preceding Statements 30-35, wherein the polymeric powder is a (meth)acrylate polymeric powder.

Statement 37: A system according to any one of the preceding Statements 30-36, wherein the polymeric powder is selected from the group consisting of polyethyl methacrylate, polymethyl methacrylate, polyethyl acrylate, polymethyl acrylate, and any combination thereof.

Statement 38: A system according to any one of the preceding Statements 30-37, wherein the polymeric powder comprises benzoyl peroxide powder.

Statement 39: A system according to any one of the preceding Statements 30-37, wherein the powdered composition further comprises benzoyl peroxide powder.

Statement 40: A system according to any one of the preceding Statements 30-39, wherein the powdered composition further comprises one or more pigments.

Statement 41: A system according to any one of the preceding Statements 30-39, wherein the polymeric powder comprises one or more pigments.

Statement 42: A system according to any one of the preceding Statements 30-41, wherein the solid amine or a solid component having an amine moiety is milled and then blended with the polymeric powder to form the powdered composition.

Statement 43: A system according to any one of the preceding Statements 30-42, wherein the solid amine or a solid component having an amine moiety comprises a powder characterized by an average particle size of from about 10 μm to about 50 μm.

Statement 44: A system according to any one of the preceding Statements 30-42, wherein the solid amine or a solid component having an amine moiety comprises a powder characterized by an average particle size that is less than about 50 μm.

Statement 45: A system according to any one of the preceding Statements 30-42, wherein the solid amine or a solid component having an amine moiety comprises a powder characterized by an average particle size that is less than about 30 μm.

Statement 46: A system according to any one of the preceding Statements 30-42, wherein the solid amine or a solid component having an amine moiety comprises a powder characterized by an average particle size that is less than about 20 μm.

Statement 47: A system according to any one of the preceding Statements 30-42, wherein the solid amine or a solid component having an amine moiety comprises a powder characterized by an average particle size that is less than about 10 μm.

Statement 48: A system according to any one of the preceding Statements 30-47, wherein the solid amine or a solid component having an amine moiety comprises from about 0.1 wt % to about 5 wt % of the powdered composition.

Statement 49: A system according to any one of the preceding Statements 30-47, wherein the solid amine or a solid component having an amine moiety comprises from about 0.1 wt % to about 1 wt % of the powdered composition.

Statement 50: A system according to any one of the preceding Statements 30-47, wherein the solid amine or a solid component having an amine moiety comprises from about 0.2 wt % to about 0.6 wt % of the powdered composition.

Statement 51: A system according to any one of the preceding Statements 30-47, wherein the solid amine or a solid component having an amine moiety comprises from about 0.25 wt % to about 0.6 wt % of the powdered composition.

Statement 52: A system according to any one of the preceding Statements 30-47, wherein the solid amine or a solid component having an amine moiety comprises from about 0.1 wt % to about 2.5 wt % of the powdered composition.

Statement 53: A system according to any one of the preceding Statements 30-52, wherein the polymeric powder comprises from about 95 wt % to about 99.9 wt % of the powdered composition.

Statement 54: A system according to any one of the preceding Statements 30-52, wherein the polymeric powder comprises from about 99.4 wt % to about 99.8 wt % of the powdered composition.

Statement 55: A system according to any one of the preceding Statements 30-52, wherein the polymeric powder comprises from about 99.5 wt % to about 99.75 wt % of the powdered composition.

Statement 56: A system according to any one of the preceding Statements 30-52, wherein the polymeric powder comprises from about 97.5 wt % to about 99.9 wt % of the powdered composition.

Statement 57: A system according to any one of the preceding Statements 30-52, wherein the polymeric powder comprises from about 99.0 wt % to about 99.9 wt % of the powdered composition.

Statement 58: A system according to any one of the preceding Statements 30-52, wherein the polymeric powder comprises from about 75 wt % to about 99.5 wt % of the powdered composition.

Statement 59: A system according to any one of the preceding Statements 30-52, wherein the polymeric powder comprises from about 65 wt % to about 95 wt % of the powdered composition.

Statement 60: A system according to any one of the preceding Statements 30-52, wherein the polymeric powder comprises from about 55 wt % to about 99 wt % of the powdered composition.

Statement 61: A kit for forming a nail coating, the kit comprising: a first container containing a powdered composition, the powdered composition comprising a polymeric powder and a solid amine or a solid component having an amine moiety; and a second container containing a liquid composition, the liquid composition comprising a cyanoacrylate monomer.

Statement 62: A kit according to Statement 61, wherein when the powdered composition in the first container is contacted with the liquid composition in the second container a nail coating is formed.

Statement 63: A kit according to Statement 61 or Statement 62, wherein the cyanoacrylate monomer is selected from the group consisting of ethyl cyanoacrylate, propyl cyanoacrylate, iso-propyl cyanoacrylate, butyl cyanoacrylate, iso-butyl cyanoacrylate, and any combination thereof.

Statement 64: A kit according to any one of the preceding Statements 61-63, wherein the cyanoacrylate monomer comprises from about 95 wt % to about 99.75 wt % of the liquid composition.

Statement 65: A kit according to any one of the preceding Statements 61-64, wherein the liquid composition further comprises an inhibitor selected from the group consisting of hydroquinone, butylated hydroxyl toluene, methoxy hydroquinone, and any combination thereof.

Statement 66: A kit according to any one of the preceding Statements 61-65, wherein the liquid composition further comprises a thickener selected from the group consisting of polyethyl methacrylate, polymethyl methacrylate, polyethyl acrylate, polymethyl acrylate, and any combination thereof.

Statement 67: A kit according to any one of the preceding Statements 61-66, wherein the solid amine or a solid component having an amine moiety is selected from the group consisting of benzyl aniline, diamino hexane, toluidine, dichloroaniline, anisidine, bromoaniline, 2-amino, 4-picoline, phenylene diamine, dihydroxy ethyl p-toluidine, barbituric acid, derivatives of barbituric acid, and any combination thereof.

Statement 68: A kit according to any one of the preceding Statements 61-67, wherein the polymeric powder is a (meth) acrylate polymeric powder.

Statement 69: A kit according to any one of the preceding Statements 61-68, wherein the polymeric powder is selected from the group consisting of polyethyl methacrylate, polymethyl methacrylate, polyethyl acrylate, polymethyl acrylate, and any combination thereof.

Statement 70: A kit according to any one of the preceding Statements 61-69, wherein the polymeric powder comprises benzoyl peroxide powder.

Statement 71: A kit according to any one of the preceding Statements 61-69, wherein the powdered composition further comprises benzoyl peroxide powder.

Statement 72: A kit according to any one of the preceding Statements 61-71, wherein the powdered composition further comprises one or more pigments.

Statement 73: A kit according to any one of the preceding Statements 61-71, wherein the polymeric powder comprises one or more pigments.

Statement 74: A kit according to any one of the preceding Statements 61-73, wherein the solid amine or a solid component having an amine moiety is milled and then blended with the polymeric powder to form the powdered composition.

Statement 75: A kit according to any one of the preceding Statements 61-74, wherein the solid amine or a solid component having an amine moiety comprises a powder characterized by an average particle size of from about 10 μm to about 50 μm.

Statement 76: A kit according to any one of the preceding Statements 61-74, wherein the solid amine or a solid component having an amine moiety comprises a powder characterized by an average particle size that is less than about 50 μm.

Statement 77: A kit according to any one of the preceding Statements 61-74, wherein the solid amine or a solid component having an amine moiety comprises a powder characterized by an average particle size that is less than about 30 μm.

Statement 78: A kit according to any one of the preceding Statements 61-74, wherein the solid amine or a solid component having an amine moiety comprises a powder characterized by an average particle size that is less than about 20 μm.

Statement 79: A kit according to any one of the preceding Statements 61-74, wherein the solid amine or a solid component having an amine moiety comprises a powder characterized by an average particle size that is less than about 10 μm.

Statement 80: A kit according to any one of the preceding Statements 61-79, wherein the solid amine or a solid component having an amine moiety comprises from about 0.1 wt % to about 5 wt % of the powdered composition.

Statement 81: A kit according to any one of the preceding Statements 61-79, wherein the solid amine or a solid component having an amine moiety comprises from about 0.1 wt % to about 1 wt % of the powdered composition.

Statement 82: A kit according to any one of the preceding Statements 61-79, wherein the solid amine or a solid component having an amine moiety comprises from about 0.2 wt % to about 0.6 wt % of the powdered composition.

Statement 83: A kit according to any one of the preceding Statements 61-79, wherein the solid amine or a solid component having an amine moiety comprises from about 0.25 wt % to about 0.6 wt % of the powdered composition.

Statement 84: A kit according to any one of the preceding Statements 61-79, wherein the solid amine or a solid component having an amine moiety comprises from about 0.1 wt % to about 2.5 wt % of the powdered composition.

Statement 85: A kit according to any one of the preceding Statements 61-84, wherein the polymeric powder comprises from about 95 wt % to about 99.9 wt % of the powdered composition.

Statement 86: A kit according to any one of the preceding Statements 61-84, wherein the polymeric powder comprises from about 99.4 wt % to about 99.8 wt % of the powdered composition.

Statement 87: A kit according to any one of the preceding Statements 61-84, wherein the polymeric powder comprises from about 99.5 wt % to about 99.75 wt % of the powdered composition.

Statement 88: A kit according to any one of the preceding Statements 61-84, wherein the polymeric powder comprises from about 97.5 wt % to about 99.9 wt % of the powdered composition.

Statement 89: A kit according to any one of the preceding Statements 61-84, wherein the polymeric powder comprises from about 99.0 wt % to about 99.9 wt % of the powdered composition.

Statement 90: A kit according to any one of the preceding Statements 61-84, wherein the polymeric powder comprises from about 75 wt % to about 99.5 wt % of the powdered composition.

Statement 91: A kit according to any one of the preceding Statements 61-84, wherein the polymeric powder comprises from about 65 wt % to about 95 wt % of the powdered composition.

Statement 92: A kit according to any one of the preceding Statements 61-84, wherein the polymeric powder comprises from about 55 wt % to about 99 wt % of the powdered composition.

Statement 93: A system according to any one of the preceding Statements 30-60, wherein the system excludes an activator in liquid form.

Statement 94: A system according to Statement 93, wherein the activator contains an amine moiety.

Statement 95: A kit according to any one of the preceding Statements 61-92, wherein the kit excludes an activator in liquid form.

Statement 96: A kit according to Statement 95, wherein the activator contains an amine moiety.

Statement 97: A composition according to any one of the preceding Statements 1-29, wherein the composition excludes an activator in liquid form.

Statement 98: A composition according to Statement 97, wherein the activator contains an amine moiety.

Statement 99: A method of forming a cosmetic nail coating, the method comprising: causing the contact of a powdered composition and a liquid composition, wherein the powdered composition and the liquid composition are contacted on a nail, and wherein the powdered composition comprises a polymeric powder and a solid amine activator or a solid component having an amine moiety activator, and the liquid composition comprises a cyanoacrylate monomer.

Statement 100: A method of forming a cosmetic nail coating, the method comprising: a) applying a liquid composition to a nail to form a wet nail, the liquid composition comprising a cyanoacrylate monomer; b) applying to the wet nail a powdered composition, the powdered composition comprising a polymeric powder and a solid amine activator or a solid activator having an amine moiety.

Statement 101: A method according to Statement 100, wherein applying to the wet nail a powdered composition comprises dipping the wet nail in the powdered composition.

Statement 102: A method according to Statement 100, wherein applying to the wet nail a powdered composition comprises sprinkling the powdered composition on the wet nail.

Statement 103: A method according to any one of the preceding Statements 100-102, further comprising repeating steps and a) and b) until a coating having a desired thickness is achieved.

Statement 104: A method according to Statement 99, wherein causing the contact of a powdered composition and a liquid composition comprises applying a liquid composition to a nail to form a wet nail and dipping the wet nail in the powdered composition.

Statement 105: A method according to Statement 99, wherein causing the contact of a powdered composition and a liquid composition comprises applying a liquid composition to a nail to form a wet nail and sprinkling the powdered composition on the wet nail.

Statement 106: A method according to any one of the preceding Statements 99-105, wherein the method excludes application of an activator in liquid form.

Statement 107: A method according to Statement 106, wherein the activator is an amine or chemical species comprising an amine moiety.

Statement 108: A method according to any one of the preceding Statements 99-107, wherein the solid amine activator or a solid activator having an amine moiety is applied to the nail in solid form.

Statement 109: A method according to any one of the preceding Statements 99-107, wherein the solid amine activator or a solid activator having an amine moiety is applied to the nail in powdered form.

Statement 110: A method according to any one of the preceding Statements 99-109, wherein the cyanoacrylate monomer is selected from the group consisting of ethyl cyanoacrylate, propyl cyanoacrylate, iso-propyl cyanoacrylate, butyl cyanoacrylate, iso-butyl cyanoacrylate, and any combination thereof.

Statement 111: A method according to any one of the preceding Statements 99-110, wherein the cyanoacrylate monomer comprises from about 95 wt % to about 99.75 wt % of the liquid composition.

Statement 112: A method according to any one of the preceding Statements 99-111, wherein the liquid composition further comprises an inhibitor selected from the group consisting of hydroquinone, butylated hydroxyl toluene, methoxy hydroquinone, and any combination thereof.

Statement 113: A method according to any one of the preceding Statements 99-112, wherein the liquid composition further comprises a thickener selected from the group consisting of polyethyl methacrylate, polymethyl methacrylate, polyethyl acrylate, polymethyl acrylate, and any combination thereof.

Statement 114: A method according to any one of the preceding Statements 99-113, wherein the solid amine activator or a solid activator having an amine moiety is selected from the group consisting of benzyl aniline, diamino hexane, toluidine, dichloroaniline, anisidine, bromoaniline, 2-amino, 4-picoline, phenylene diamine, dihydroxy ethyl p-toluidine, barbituric acid, derivatives of barbituric acid, and any combination thereof.

Statement 115: A method according to any one of the preceding Statements 99-114, wherein the polymeric powder is a (meth)acrylate polymeric powder.

Statement 116: A method according to any one of the preceding Statements 99-115, wherein the polymeric powder is selected from the group consisting of polyethyl methacrylate, polymethyl methacrylate, polyethyl acrylate, polymethyl acrylate, and any combination thereof.

Statement 117: A method according to any one of the preceding Statements 99-116, wherein the polymeric powder comprises benzoyl peroxide powder.

Statement 118: A method according to any one of the preceding Statements 99-117, wherein the powdered composition further comprises benzoyl peroxide powder.

Statement 119: A method according to any one of the preceding Statements 99-118, wherein the powdered composition further comprises one or more pigments.

Statement 120: A method according to any one of the preceding Statements 99-118, wherein the polymeric powder comprises one or more pigments.

Statement 121: A method according to any one of the preceding Statements 99-120, wherein the solid amine activator or a solid activator having an amine moiety is milled and then blended with the polymeric powder to form the powdered composition.

Statement 122: A method according to any one of the preceding Statements 99-121, wherein the solid amine activator or a solid activator having an amine moiety comprises a powder characterized by an average particle size of from about 10 μm to about 50 μm.

Statement 123: A method according to any one of the preceding Statements 99-121, wherein the solid amine activator or a solid activator having an amine moiety comprises a powder characterized by an average particle size that is less than about 50 μm.

Statement 124: A method according to any one of the preceding Statements 99-121, wherein the solid amine activator or a solid activator having an amine moiety comprises a powder characterized by an average particle size that is less than about 30 μm.

Statement 125: A method according to any one of the preceding Statements 99-121, wherein the solid amine activator or a solid activator having an amine moiety comprises a powder characterized by an average particle size that is less than about 20 μm.

Statement 126: A method according to any one of the preceding Statements 99-121, wherein the solid amine activator or a solid activator having an amine moiety comprises a powder characterized by an average particle size that is less than about 10 μm.

Statement 127: A method according to any one of the preceding Statements 99-126, wherein the solid amine activator or a solid activator having an amine moiety comprises from about 0.1 wt % to about 5 wt % of the powdered composition.

Statement 128: A method according to any one of the preceding Statements 99-126, wherein the solid amine activator or a solid activator having an amine moiety comprises from about 0.1 wt % to about 1 wt % of the powdered composition.

Statement 129: A method according to any one of the preceding Statements 99-126, wherein the solid amine activator or a solid activator having an amine moiety comprises from about 0.2 wt % to about 0.6 wt % of the powdered composition.

Statement 130: A method according to any one of the preceding Statements 99-126, wherein the solid amine activator or a solid activator having an amine moiety comprises from about 0.25 wt % to about 0.6 wt % of the powdered composition.

Statement 131: A method according to any one of the preceding Statements 99-126, wherein the solid amine activator or a solid activator having an amine moiety comprises from about 0.1 wt % to about 2.5 wt % of the powdered composition.

Statement 132: A method according to any one of the preceding Statements 99-131, wherein the polymeric powder comprises from about 95 wt % to about 99.9 wt % of the powdered composition.

Statement 133: A method according to any one of the preceding Statements 99-131, wherein the polymeric powder comprises from about 99.4 wt % to about 99.8 wt % of the powdered composition.

Statement 134: A method according to any one of the preceding Statements 99-131, wherein the polymeric powder comprises from about 99.5 wt % to about 99.75 wt % of the powdered composition.

Statement 135: A method according to any one of the preceding Statements 99-131, wherein the polymeric powder comprises from about 97.5 wt % to about 99.9 wt % of the powdered composition.

Statement 136: A method according to any one of the preceding Statements 99-131, wherein the polymeric powder comprises from about 99.0 wt % to about 99.9 wt % of the powdered composition.

Statement 137: A method according to any one of the preceding Statements 99-131, wherein the polymeric powder comprises from about 75 wt % to about 99.5 wt % of the powdered composition.

Statement 138: A method according to any one of the preceding Statements 99-131, wherein the polymeric powder comprises from about 65 wt % to about 95 wt % of the powdered composition.

Statement 139: A method according to any one of the preceding Statements 99-131, wherein the polymeric powder comprises from about 55 wt % to about 99 wt % of the powdered composition.

We claim:

1. A system for forming a nail coating, the system comprising:
   a powdered composition comprising a polymeric powder and as an activator a solid amine or a solid component having an amine moiety, wherein the polymeric powder comprises from about 75 wt % to about 99.5 wt % of the powdered composition and the solid amine or the solid component having an amine moiety comprises from about 0.1 wt % to about 5 wt % of the powdered composition; and
   a liquid composition comprising a cyanoacrylate monomer, wherein the cyanoacrylate monomer comprises from about 95 wt % to about 99.75 wt % of the liquid composition;
   wherein when the powdered composition is contacted with the liquid composition a nail coating is formed;
   wherein the powdered composition excludes the activator in liquid form; and
   wherein the solid amine or the solid component having an amine moiety is selected from the group consisting of benzyl aniline, diaminohexane, toluidine, dichloroaniline, anisidine, bromoaniline, 2-amino-4-picoline, phenylene diamine, dihydroxy ethyl p-toluidine, barbituric acid, derivatives of barbituric acid, and any combination thereof.

2. The system according to claim 1, wherein the cyanoacrylate monomer is selected from the group consisting of ethyl cyanoacrylate, propyl cyanoacrylate, iso-propyl cyanoacrylate, butyl cyanoacrylate, iso-butyl cyanoacrylate, and any combination thereof.

3. The system according to claim 1, wherein the liquid composition further comprises an inhibitor selected from the group consisting of hydroquinone, butylated hydroxyl toluene, methoxy hydroquinone, and any combination thereof.

4. The system according to claim 3, wherein the liquid composition further comprises a thickener selected from the group consisting of polyethyl methacrylate, polymethyl methacrylate, polyethyl acrylate, polymethyl acrylate, and any combination thereof.

5. The system according to claim 4, wherein the polymeric powder is a (meth)acrylate polymeric powder.

\* \* \* \* \*